(12) United States Patent
Bergmann et al.

(10) Patent No.: US 7,763,435 B2
(45) Date of Patent: Jul. 27, 2010

(54) METHOD FOR DIAGNOSIS OF ALZHEIMER'S DISEASE WITH DETERMINATION OF LASP-1 IMMUNOREACTIVITY

(75) Inventors: Andreas Bergmann, Berlin (DE); Christina Fischer-Schulz, Berlin (DE); Joachim Struck, Berlin (DE)

(73) Assignee: B.R.A.H.M.S. Aktiengesellschaft, Hennigsdorf (DE)

(*) Notice: Subject to any disclaimer, the term of this patent is extended or adjusted under 35 U.S.C. 154(b) by 97 days.

(21) Appl. No.: 12/041,370

(22) Filed: Mar. 3, 2008

(65) Prior Publication Data
US 2008/0248509 A1 Oct. 9, 2008

Related U.S. Application Data

(62) Division of application No. 10/511,758, filed as application No. PCT/EP03/03940 on Apr. 15, 2003, now Pat. No. 7,405,049.

(30) Foreign Application Priority Data
Apr. 19, 2002 (EP) .................................. 02008840

(51) Int. Cl.
*G01N 33/53* (2006.01)
(52) U.S. Cl. ...................................... 435/7.1; 435/7.94
(58) Field of Classification Search ....................... None
See application file for complete search history.

(56) References Cited

U.S. PATENT DOCUMENTS

| 4,822,733 | A | 4/1989 | Morrison |
|---|---|---|---|
| 5,512,493 | A | 4/1996 | Mathis et al. |
| 5,639,617 | A | 6/1997 | Bohuon |
| 5,981,218 | A | 11/1999 | Rio et al. |
| 6,756,483 | B1 | 6/2004 | Bergmann |
| 7,132,246 | B2 | 11/2006 | Bergmann et al. |
| 7,157,081 | B2 | 1/2007 | Bergmann et al. |
| 2003/0219745 | A1* | 11/2003 | Tang et al. ...................... 435/6 |
| 2004/0044181 | A1* | 3/2004 | Tang et al. .................. 530/350 |
| 2005/0059104 | A1 | 3/2005 | Bergmann et al. |
| 2005/0064506 | A1 | 3/2005 | Bergmann et al. |
| 2005/0074811 | A1 | 4/2005 | Bergmann et al. |
| 2005/0106645 | A1 | 5/2005 | Bergmann et al. |
| 2005/0239150 | A1 | 10/2005 | Bergmann et al. |
| 2006/0035221 | A1 | 2/2006 | Bergmann et al. |
| 2006/0115869 | A1 | 6/2006 | Bergmann et al. |
| 2006/0234295 | A1 | 10/2006 | Bergmann et al. |

FOREIGN PATENT DOCUMENTS

| DE | 42 27 454 C1 | 3/1994 |
|---|---|---|
| DE | 198 47 690 A1 | 4/2000 |
| DE | 199 15 485 A1 | 10/2000 |
| EP | 0 539 477 B1 | 8/1995 |
| EP | 0 656 121 B1 | 4/1998 |
| WO | WO 92/10200 | 6/1992 |
| WO | WO 98/27213 | 6/1998 |
| WO | WO 00/22439 | 4/2000 |
| WO | WO 01/25268 | 4/2001 |
| WO | WO 01/36975 | 5/2001 |
| WO | WO 01/85986 | 11/2001 |
| WO | WO 01/86288 | 11/2001 |
| WO | WO 02/00857 | 1/2002 |
| WO | WO 02/10771 | 2/2002 |

OTHER PUBLICATIONS

Growdon, "Biomarkers of Alzheimer Disease." Arch Neurol, 1999, 56(3): 281-283.*
Torian et al., Int Psychogeriatr. 1992; 4: 231-9.*
Ernst et al., J. Neuroimmunol. 2007; 189: 169-174.*
Lib et al., Analytical Biochem. 2003; 314: 121-127.*
Balin et al., JAOA. 2001; 101: S1-S6.*
Office Action dated Sep. 24, 2007 in co-pending U.S. Appl. No. 10/496,173.
Office Action dated Sep. 4, 2007 in co-pending U.S. Appl. No. 10/496,096.
Supplemental Notice of Allowability in co-pending U.S. Appl. No. 10/511,756.
Office Action dated Jun. 27, 2007 in co-pending U.S. Appl. No. 10/496,250.
Office Action dated Jan. 7, 2008 in co-pending U.S. Appl. No. 10/497,679.
Office Action dated Jan. 29, 2008 in co-pending U.S. Appl. No. 10/516,618.
Reinhart, K. et al., "Sepsis und septischer Schock," Need Pub Name (2001) pp. 756-760.
Schreiber, V. et al., "Lasp-1, a Novel Type of Actin-Binding Protein Accumulating in Cell Membrane Extensions," *Molecular Medicine*, vol. 4 (1998) pp. 675-687.

(Continued)

*Primary Examiner*—Bridget E Bunner
*Assistant Examiner*—Christina Borgeest
(74) *Attorney, Agent, or Firm*—Heslin Rothenberg Farley & Mesiti P.C.

(57) ABSTRACT

Method for early diagnosis and diagnosis, for prognosis and assessment of the severity and for therapy-accompanying monitoring of inflammatory diseases and infections, in particular sepsis-like systemic infections and Alzheimer's disease, in which the presence and/or amount of the protein LASP-1 (SEQ ID NO:1) or of the protein LAP-1 (SEQ ID NO:16) or of an immunoreactive fragment of one of these proteins in free and/or protein-bound form is determined, preferably as immunoreactivity, in a biological fluid, or optionally a tissue sample, of a patient, and conclusions are drawn with respect to the presence, the expected course, the severity or the success of a therapy of the inflammatory disease or of the infection from the presence and/or amount of the proteins determined.

7 Claims, 6 Drawing Sheets

OTHER PUBLICATIONS

Figure 1:
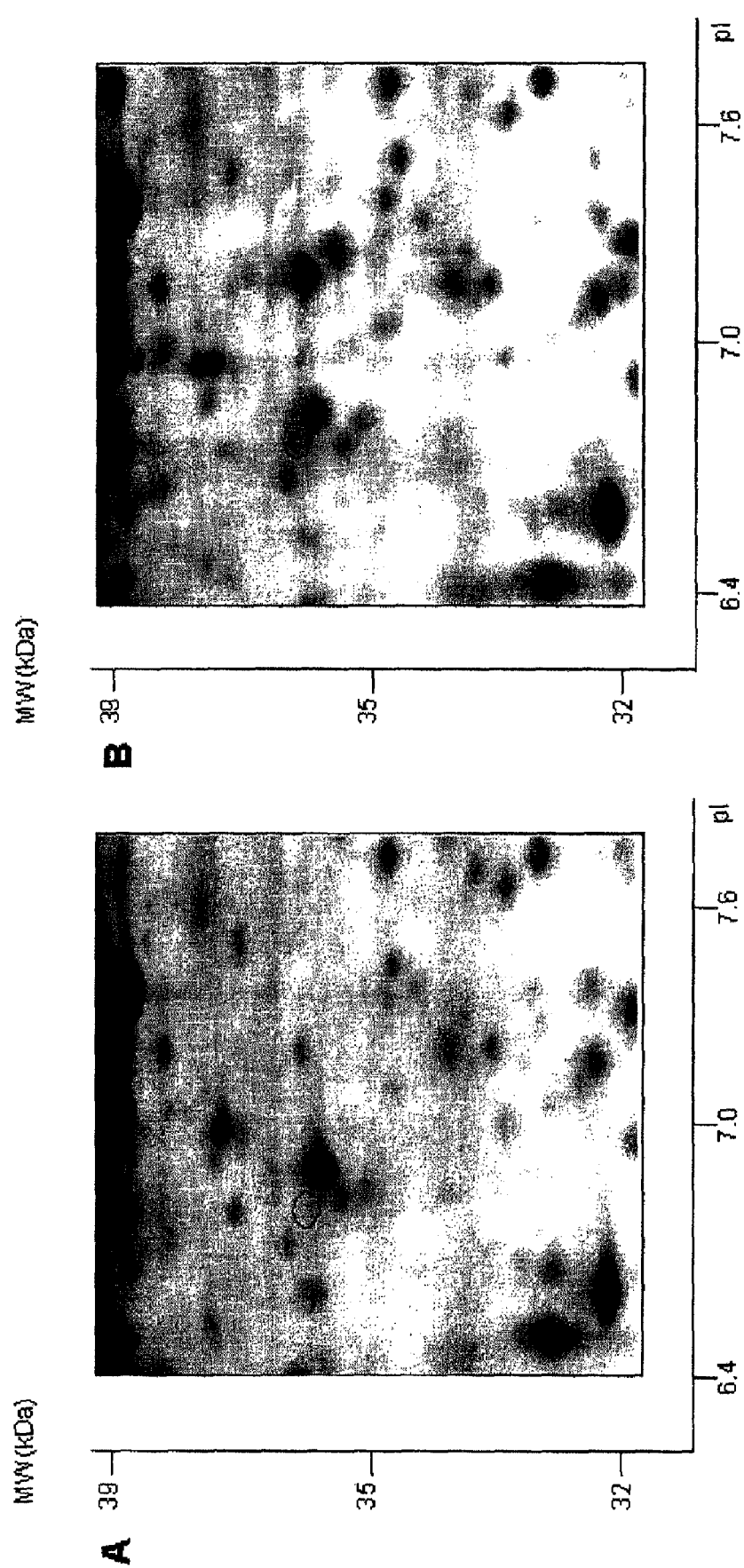

Butt, E. et al., "Actin Binding of Human LIM and SH3 Protein Is Regulated by cGMP- and cAMP-dependent Protein Kinase Phosphorylation on Serine 146*," *The Journal of Biological Chemistry*, vol. 278, No. 18 (May 2, 2003) pp. 15601-15607.

Beishuizen, A. et al., "Endogenous Mediators in Sepsis and Septic Shock," *Advances in Clinical Chemistry*, vol. 33 (1998) pp. 55-131.

Gabay, C. et al., "Acute-Phase Proteins and Other Systemic Responses to Inflammation," *The New England Journal of Medicine*, vol. 340, No. 6 (Feb. 11, 1999) pp. 448-454.

Assicot, M. et al., "High serum procalcitonin concentrations in patients with sepsis and infection," *The Lancet*, vol. 341, No. 8844 (Feb. 27, 1993) pp. 515-518.

Karzai, W. et al., "Procalcitonin—A New Indicator of the Systemic Response to Severe Infections," *Infection*, vol. 25, No. 6 (Nov. 1997) pp. 329-334.

Oczenski, W. et al., "Procalcitonin: a new parameter for the diagnosis of bacterial infection in the peri-operative period," *European Journal of Anaesthesiology*, vol. 15 (1998) pp. 202-209.

Redl, H. et al., "Procalcitonin release patterns in a baboon model of trauma and sepsis: Relationship to cytokines and neopterin," *Crit Care Med*, vol. 28, No. 11 (2000) pp. 3659-3663.

Redl, H. et al., "Non-Human Primate Models of Sepsis," *Sepsis*, vol. 2 (1998) pp. 243-253.

Panacek, E., "Anti-TNF strategies," Journal für Anästhesie (2001) pp. 4-5.

Calandra, T. et al., "Protection from septic shock by neutralization of macrophage migration inhibitory factor," *Nature Medicine*, vol. 6, No. 2 (Feb. 2000) pp. 164-170.

Garber, K., "Protein C may be sepsis solution," *Nature Biotechnology*, vol. 18 (Sep. 2000) pp. 917-918.

Chew, C. et al., "Lasp-1 is a regulated phosphoprotein within the cAMP signaling pathway in the gastric parietal cell," *The American Psychological Society*, vol. 275 (1998) pp. 56-67.

Tomasetto, C. et al., "Lasp-1 (MLN 50) defines a new LIM protein subfamily characterized by the association of LIM and SH3 domains," *FEBS Letters*, vol. 373 (1995) pp. 245-249.

Tomasetto, C. et al., "Identification of Four Novel Human Genes Amplified and Overexpressed in Breast Carcinoma and Localized to the q11-q21.3 Region of Chromosome 17," *Genomics*, vol. 28 (1995) pp. 367-376.

Lue, L. et al., "Inflammatory Repertoire of Alzheimer's Disease and Nondemented Elderly Microglia In Vitro," *GLIA*, vol. 35 (2001) pp. 72-79.

Hüll, M. et al., "Anti-inflammatory substances—a new therapeutic option in Alzheimer's disease," *DDT*, vol. 4, No. 6 (Jun. 1999) pp. 275-282.

Licastro, F. et al., "Increased plasma levels of interleukin-1, interleukin-6 and α-1-antichymotrypsin in patients with Alzheimer's disease: peripheral inflammation or signals from the brain?," *Journal of Neuroimmunology*, vol. 103 (2002) pp. 97-102.

Akiyama, H. et al., "Inflammation and Alzheimer's disease," *Neurobiology of Aging*, vol. 21 (2000) pp. 383-421.

Hüll, M. et al., "Anti-inflammatory drugs: a hope for Alzheimer's disease?," *Exp. Opin. Invest. Drugs*, vol. 9, No. 4 (2002) pp. 671-683.

Hüll, M. et al., "Inflammatory mechanisms in Alzheimer's disease," *Eur Arch Psychiatry Clin Neurosci*, vol. 246 (1996) pp. 124-128.

Rhodin, J. et al., "Animal Model of Alzheimer-like Vascular Pathology and Inflammatory Reaction," *Annals New York Academy of Sciences*, pp. 345-352.

Schreiber, V. et al., "Lasp-1, a Novel Type of Actin-Binding Protein Accumulating in Cell Membrane Extensions," *Molecular Medicine*, vol. 4 (1998) pp. 675-687.

Ghillani, P. et al., "Monoclonal Antipeptide Antibodies as Tools to Dissect Closely Related Gene Products," *The Journal of Immunology*, vol. 141, No. 9 (Nov. 1, 1998) pp. 3156-3163.

Ghillani, P. et al., "Identification and Measurement of Calcitonin Precursors in Serum of Patients with Malignant Diseases," *Cancer Research*, vol. 49, No. 23 (Dec. 1, 1989) pp. 6845-6851.

Otto, A. et al., "Identification of human myocardial proteins separated by two-dimensional electrophoresis using an effective sample preparation for mass spectometry," *Electrophoresis*, vol. 17 (1996) pp. 1643-1650.

Neubauer, G. et al., "Mass spectrometry and EST-database searching allows characterization of the multi-protein spliceosome complex," *Nature Genetics*, vol. 20 (Sep. 1998) pp. 46-50.

Lingner, J. et al., "Reverse Transcriptase Motifs in the Catalytic Subunit of Telomerase," *Science*, vol. 276 (Apr. 25, 1997) pp. 561-567.

Mann, M. et al., "Use of mass spectrometry-derived data to annotate nucleotide and protein sequence databases," *TRENDS in Biochemical Sciences* vol. 26, No. 1 (Jan. 2001) pp. 54-61.

International Search Report for PCT/EP03/03946 dated Nov. 10, 2003.

* cited by examiner

- Controls n=294 4,4 % positive
- Alzheimer's disease n=80 86,3% positive

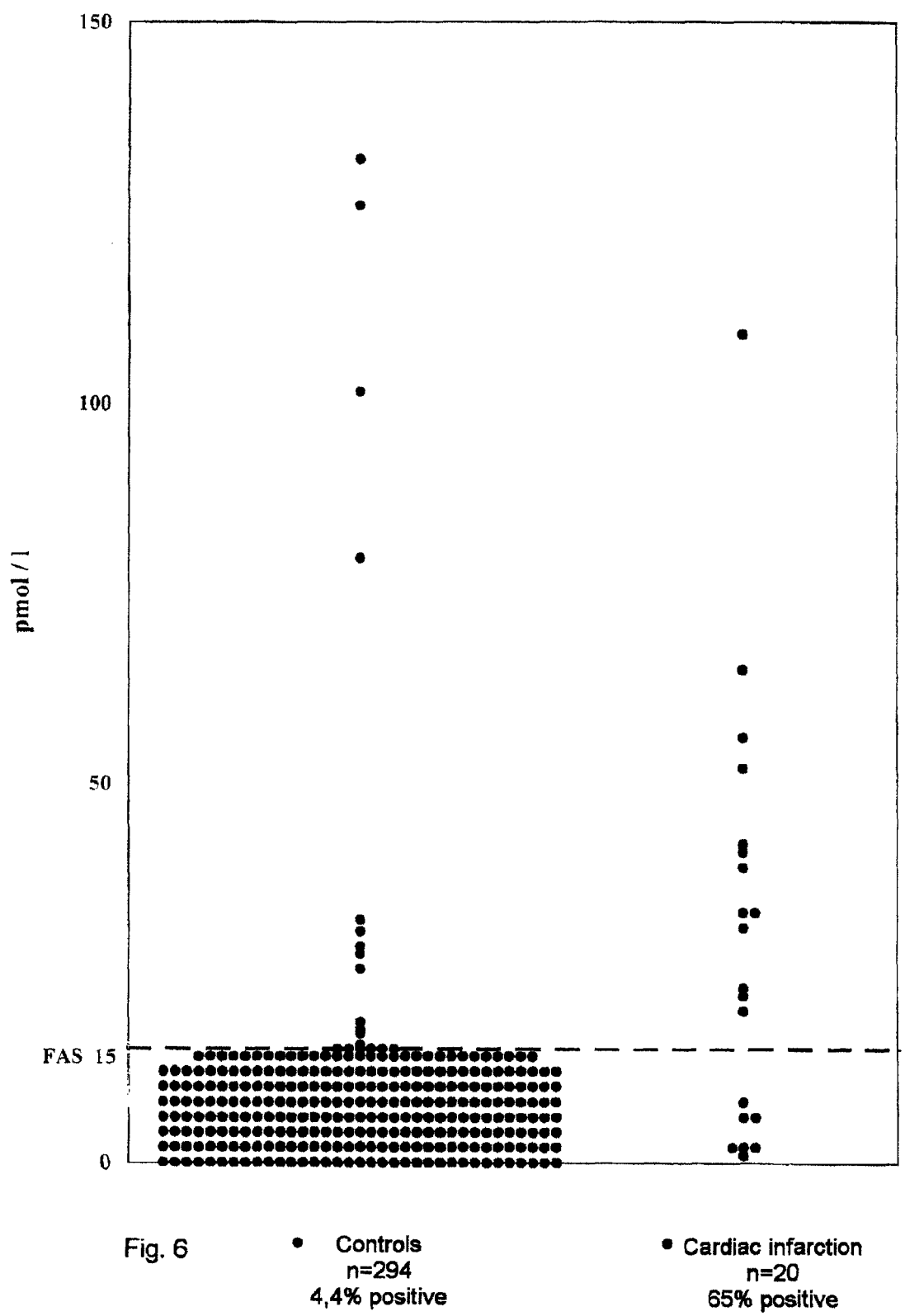
Fig. 6  • Controls  n=294  4,4% positive    • Cardiac infarction  n=20  65% positive

METHOD FOR DIAGNOSIS OF ALZHEIMER'S DISEASE WITH DETERMINATION OF LASP-1 IMMUNOREACTIVITY

This application is a divisional of U.S. application Ser. No. 10/511,758, filed May 25, 2005 now U.S. Pat. No. 7,405,049, which is a §371 filing of International Application PCT/EP03/03940, filed Apr. 15, 2003 (published as WO 03/089934), which claims benefit of European Application No. 02008840.7 filed Apr. 19, 2002. The entire content of each of the prior applications is incorporated herein by reference.

The present invention relates to novel uses of the protein LASP-1 and any closely related proteins which, at least with regard to their first 200 amino acids, have substantially the same sequence as LASP-1 and hence a comparable immunoreactivity, and of fragments thereof, for the medical diagnosis of inflammatory diseases and infections, in particular of sepsis and sepsis-like systemic infections and of inflammatory diseases which are localized in the brain or which extend to the brain. It is based on the detection for the first time of greatly increased concentrations of the protein LASP-1 in the brain tissue of primates in which a sepsis or systemic inflammation was induced experimentally by toxin administration, and on the subsequent detection of a greatly increased LASP-1 immunoreactivity in the circulation of patients suffering from sepsis and of Alzheimer patients, and an increased corresponding immunoreactivity also being found in patients suffering from cardiac infarction.

Where, in the following description, the term LASP-1 is used, this term is intended to denote not only the known protein LASP-1 having the specific amino acid sequence specified in SEQ ID NO:1 but also any related proteins which have an identical sequence to this LASP-1 over wide ranges, for example the protein LAP-1, explanatory statements about such proteins appearing at the end of the experimental section of this Application. This definition applies to all references to LASP-1, unless something else is evident from the specific context for a person skilled in the art. When the term LASP-1 is used, this term also means fragments having an LASP-1 immunoreactivity, it being possible for all stated products to be present both in free form and optionally in a form bound to binding proteins and/or in a posttranslationally modified form, for example in glycosylated and/or phosphorylated form.

The present invention has its origin in intensive research work by the Applicant in relation to further improvements of the diagnosis and therapy of inflammations and infections.

Inflammations are defined very generally as certain physiological reactions of an organism to different types of external effects, such as, for example, injuries, burns, allergens, infections by microorganisms, such as bacteria and fungi and viruses, to foreign tissues which trigger rejection reactions, or to certain endogenous states of the body which trigger inflammation, for example in autoimmune diseases and cancer. Inflammations may occur as harmless, localized reactions of the body but are also typical features of numerous serious chronic and acute diseases of individual tissues, organs, organ parts and tissue parts.

Local inflammations are generally part of the healthy immune response of the body to harmful effects, and hence part of the life-preserving defense mechanism of the organism. However, if inflammations are part of a misdirected response of the body to certain endogenous processes, such as, for example, in autoimmune diseases, and/or are of a chronic nature, or if they reach systemic extents, as in the case of systemic inflammatory response syndrome (SIRS) or in a severe sepsis caused by infection, the physiological processes typical of inflammatory reactions go out of control and become the actual, frequently life-threatening pathological process. In the context of the present patent application, Alzheimer's disease, which is characterized by an unstoppable progressive corticocerebral atrophy occurring as a rule in the 5th to 6th decade of life and, owing to its frequency, is of major economic importance, is also regarded as a disease which is accompanied by typical symptoms of an inflammation, in particular of the brain.

It is now known that the origin and the course of inflammatory processes are controlled by a considerable number of substances which are predominantly of a protein or peptide nature, or are accompanied by the occurrence of certain biomolecules for a more or less limited time. The endogenous substances involved in inflammatory reactions include in particular those which can be assigned to the cytokines, mediators, vasoactive substances, acute phase proteins and/or hormonal regulators. The inflammatory reaction is a complex physiological reaction in which both endogenous substances activating the inflammatory process (e.g. TNF-α, interleukin-1) and deactivating substances (e.g. interleukin-10) are involved.

In systemic inflammations, as in the case of sepsis or of septic shock, the inflammation-specific reaction cascades spread in an uncontrolled manner over the whole body and become life-threatening in the context of an excessive immune response. Regarding the current knowledge about the occurrence and the possible role of individual groups of endogenous inflammation-specific substances, reference is made, for example, to A. Beishuizen et al., "Endogenous Mediators in Sepsis and Septic Shock", Advances in Clinical Chemistry, Vol. 33, 1999, 55-131; and C. Gabay et al., "Acute Phase Proteins and Other Systemic Responses to Inflammation", The New England Journal of Medicine, Vol. 340, No. 6, 1999, 448-454. Since the understanding of sepsis and related systemic inflammatory diseases, and hence also recognized definitions, have changed in recent years, reference is also made to K. Reinhart et al., "Sepsis und septischer Schock" [Sepsis and Septic Shock], in: Intensiv-medizin, Georg Thieme Verlag, Stuttgart, N.Y., 2001, 756-760, where a modern definition of sepsis is given. In the context of the present Application, the terms sepsis and inflammatory diseases used are based on the definitions as given in the three stated references.

Whereas at least in Europe the systemic bacterial infection detectable by a positive blood culture long characterized the term sepsis, sepsis is now primarily understood as being systemic inflammation which is caused by infection but, as a pathological process, has considerable similarities with systemic inflammations which are triggered by other causes. Said transformation in the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known or presumed to be involved in an inflammatory process, the ones which are suitable for diagnostic purposes are in particular those whose occurrence is very specific for inflammatory diseases or certain phases or severities of inflammatory diseases, whose concentrations change in a dramatic and diagnostically significant manner and which moreover have the stabilities required for routine determinations and reach high concentration values. For diagnostic purposes, the reliable correlation of pathological process (inflammation, sepsis) with the respective biomarker is of primary importance (good specificity and selectivity, without there being any need to know its role in the complex cascade of the endogenous substances involved in the inflammatory process.

A known endogenous substance which is particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis or for early distinguishing of a sepsis caused by infection from severe inflammations which have other causes. The determination of procalcitonin as a sepsis marker is the subject of the publication by M. Assicot et al., "High serum procalcitonin concentrations in patients with sepsis and infection", The Lancet, Vol. 341, No. 8844, 1993, 515-518; and the patents DE 42 27 454 C2 and EP 0 656 121 B1 and U.S. Pat. No. 5,639,617. Reference is hereby made to said patents and to early literature references mentioned in said publications for supplementing the present description. In recent years, the number of publications on the subject of procalcitonin has greatly increased. As typical of recent published reviews, reference is also therefore made to W. Karzai et al., "Procalcitonin—A New Indicator of the Systemic Response to Severe Infection", Infection, Vol. 25, 1997, 329-334; and M. Oczenski et al., "Procalcitonin: a new parameter for the diagnosis of bacterial infection in the peri-operative period", European Journal of Anesthesiology 1998, 15, 202-209; and furthermore H. Redl et al., "Procalcitonin release patterns in a baboon model of trauma and sepsis: Relationship to cytokines and neopterin", Crit Care Med 2000, Vol. 28, No. 11, 3659-3663; and H. Redl et al., "Non-Human Primate Models of Sepsis", in: Sepsis 1998; 2:243-253; and the further literature references cited therein.

The availability of the sepsis marker procalcitonin has given considerable impetus to sepsis research, and intensive efforts are now being made to find further biomarkers which can supplement the procalcitonin determination and/or are capable of providing additional information for purposes of fine diagnosis or differential diagnosis. The search for potential novel sepsis biomarkers is, however, complicated by the fact that frequently very little or nothing is known about the exact function or about the exact reasons for the occurrence of certain endogenous substances which are involved in the inflammatory or sepsis process.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin is increased but also significantly increased concentrations can be observed for other peptide substances which have prohormone immunoreactivity. While the phenomenon described is well documented, the causes of the increase in the prohormone immunoreactivity in sepsis are still substantially unexplained.

In the present Application, the results of another fruitful, purely experimental approach in the search for further inflammation- or sepsis-specific biomolecules is reported. These experimental investigations, too, originate from the determination of procalcitonin in relation to systemic inflammatory reactions of infectious aetiology. Thus, it had been observed at a very early stage that, in sepsis, the procalcitonin is evidently not formed in the same way as when it is a precursor for the hormone calcitonin. Thus, high procalcitonin levels were also observed in patients whose thyroid had been removed. The thyroid therefore cannot be the organ in which procalcitonin is formed or secreted during sepsis. In the publications by H. Redl et al., "Procalcitonin release patterns in a baboon model of trauma and sepsis: Relationship to cytokines and neopterin", Crit Care Med 2000, Vol. 28, No. 11, 3659-3663; and H. Redl et al., "Non-Human Primate Models of Sepsis", Sepsis 1998; 2:243-253, the results of experimental investigations which are intended to clarify the formation of procalcitonin in sepsis are reported. In said papers, an artificial sepsis is induced by endotoxin administration to primates (baboons), and the experimentally induced states in which the highest procalcitonin concentrations in the blood are reached are determined. In the context of the present Application, a further development of the experimental animal model described in said papers serves for determining novel endogenous inflammation- and/or sepsis-specific biomarkers of a peptide or protein nature, the occurrence of which is characteristic of sepsis or certain forms of inflammation and/or sepsis and which therefore permit a specific, optionally organ-specific, sepsis or inflammation diagnosis. The primate model was chosen on the basis of the very considerable similarity of the physiology of primates and humans and the high cross-reactivity with many therapeutic and diagnostic human reagents.

Since the endogenous substances formed during inflammations are part of the complex reaction cascade of the body, not only are such substances also of diagnostic interest but attempts are also currently being made, with considerable effort, to intervene therapeutically in the inflammatory process by influencing the origin and/or the concentration of individual substances of this type, in order to stop at as early a stage as possible the systemic spread of the inflammation which is observed, for example, in sepsis. In this context, endogenous substances which can be shown to be involved in the inflammatory process are also to be regarded as potential therapeutic targets. Attempts starting from certain mediators of the inflammatory process to positively influence said process therapeutically are described, for example, in E. A. Panacek, "Anti-TNF strategies", Journal für Anästhesie und Intensivbehandlung; No. 2, 2001, 4-5; T. Calandra et al., "Protection from septic shock by neutralization of macrophage migration inhibitory factor", Nature Medicine, Vol. 6, No. 2, 2000, 164-170; or K. Garber, "Protein C may be sepsis solution", Nature Biotechnology, Vol. 18, 2000, 917-918. In view of the fairly disappointing therapeutic approaches to date, there is considerable interest in identifying endogenous biomolecules which, are as inflammation- or sepsis-specific as possible and, as therapeutic targets, also open up new prospects for success for the therapeutic control of inflammation.

The present invention is based on the fact that, in primates and humans, the greatly overexpressed protein LASP-1 or a protein which is identical to it over large N-terminal sequence segments is detectable in a soluble form in inflammations caused by infections in cytoplasmic brain tissue, in particular in contrast to healthy persons or untreated persons in whom it is not found or is found only in concentrations at the analytical limit of detection, but also in contrast to other body tissues of septic primate experimental animals, making this protein appear suitable for diagnosing inflammation and diagnosing infection or sepsis where the brain is involved.

The invention is furthermore based on the fact that it was found that substantially increased LASP-1 immunoreactivity is measurable also in the circulation of human sepsis patients, but also of Alzheimer patients, underlining or greatly enhancing the value of the knowledge gained on the basis of brain extracts of primates.

The uses in diagnosis, which arise owing to the detection for the first time of the brain-specific occurrence of LASP-1 in the experimental simulation of inflammations on sepsis and the detection of a substantially increased LASP-1 immunoreactivity in the circulation, are described in more detail below.

As mentioned in more detail below in the experimental section, the starting point of the invention was the finding that, after experimental triggering of an artificial sepsis in baboons by endotoxin administration (LPS from *Salmonella Typhimurium*) and working-up of brain tissue of the treated animals by 2D gel electrophoresis, a protein which was substantially identical, and in particular at least over the segment of the amino acids from 1 to 200, to the known protein LASP-1 was found as one of the products identifiable only in the treated animals, the protein moreover being observed in considerably increased concentration only in the brain tissue. For its identification, a new protein spot, which was found only in the brain tissue of the treated animals and, according to gel electrophoresis, had a molecular weight of about 36±3 kDa and an isoelectric point of about 6.6-7.0, was isolated from the electrophoresis gel and separated into fragments by trypsin digestion, said fragments being analyzed in a manner known per se by mass spectrometry. By comparison with the known mass spectrum of the trypsin-treated protein LASP-1, the protein of the isolated spot was identified as a protein which was identical to the protein LASP-1 at least over wide segments.

The identification of the product found in the protein spot is described in more detail in the experimental section, and the identification described is to be regarded, according to recognized principles of interpretation, as the safe identification of a product having an amino acid sequence of the protein LASP-1.

The theoretically determined molecular weight of the peptide chain of LASP-1 (cf. SEQ ID NO:1; 261 amino acids) is 29,717 Dalton. LASP-1 is, however, present physiologically in a posttranslationally processed form (glycosylated and phosphorylated). Thus, the product subsequently defined as LASP-1 was originally identified as a 40 kDa cAMP-dependent phosphoprotein ("pp 40") in stomach wall cells (cf. C. S. Chew et al., Journal of Cell Science 113, 2035-2045 (2000); C. S. Chew et al., Am. J. Physiol. 275 (Cell Physiol. 44): C56-C67, (1998)).

The amino acid sequence of the phosphoprotein defined as LASP-1 was originally determined as that of the putative express product of the cDNA of a gene "MLN 50" from the range q11-q21.3 of chromosome 17, which gene is overexpressed in human breast cancer cell lines (C. Tomasetto et al., FEBS Letters 373 (1995): 245-249; C. Tomasetto et al., Genomics 28: 367-376 (1995); I. Bièche et al., Cancer Res. 56: 3886-3890 (1996)). The name LASP-1 is attributable to the fact that, in this protein, for the first time a so-called LIM domain (a Zn-binding domain known from various proteins; cf. A. Hammarström et al., Biochemistry 1996; 35, 12723-12732) is combined with a domain (SH3) known from the receptor-independent so-called src kinase, a tyrosine kinase (LIM and SH3 Protein); cf. also Brian K. Kay et al., FASEB J. 14, 231-241 (2000).

LASP-1 mRNA is detectable everywhere in normal cells (e.g. prostate, liver, muscle, brain, various cell types) and is overexpressed in a certain percentage of breast cancer cases. It was found that LASP-1 is an actin-binding protein which is assumed to belong to the proteins associated with the cytoskeleton and to be important for the cell shape and cell mobility and possibly the signal transmission. It is also detectable in nerve endings. LASP-1 is solubilized by detergents only with difficulty. In vitro, LASP-1 has proved to be a substrate which can be outstandingly phosphorylated with the cAMP-dependent serine-threonine kinase PKA. LASP-1 has different expression patterns in different epithelium cell types (cf. C. S. Chew et al., Journal of Cell Science 113, 2035-2045 (2000); C. S. Chew et al., Am. J. Physiol. 275 (Cell Physiol. 44): C56-C67, (1998)).

The occurrence of LASP-1 or of a protein substantially corresponding thereto in overexpressed form in the brain tissue in sepsis is of considerable scientific, diagnostic and possibly also therapeutic interest. The fact that LASP-1 is a kinase substrate and phosphoprotein lends it a certain similarity to the so-called tau-proteins, which play a role, particularly for diagnostic purposes, in Alzheimer's disease (cf. for example G. A. Jicha et al., Journal of Neurochemistry, 69, 2087-2095 (1997) and the literature cited therein; and EP 637 418; EP 737 208; EP 772 634; EP 610 330; and EP 618 968).

It is now well known that Alzheimer's disease can be regarded as a brain-specific inflammatory process without there being any intention thereby to make a statement regarding the cause of the disease or consequence of the disease (Lih-Fen Lue et al., GLIA 35:72-79, 2001; Michael Hüll et al., DDT Vol. 4, No. 6: 275-282; (June 1999); F. Licastro et al., Journal of Neuroimmunology 103 (2000), 97-102; Neuroinflammation Working Group Haruhiko Akiyama et al., Neurobiology of Aging 21 (2000) 383-421; Michael Hull et al., Exp. Opin. Invest. Drugs (2000) 9(4):671-683; M. Hüll et al., Eur Arch Psychiatry Clin Neurosci (1996) 246:124-128; J. Rhodin et al., Annals New York Academy of Sciences, 199x, 345-352). The fact that the phosphoprotein LASP-1 or a protein substantially corresponding thereto is detectable in overexpressed form specifically in the brain under experimental conditions which simulate a sepsis or a systemic inflammation process made it very probable that overexpression of LASP-1 or of a certain expression form of LASP-1 is observable also in Alzheimer's disease, and the determination of LASP-1 is therefore also of importance for diagnosing Alzheimer' disease. Subsequently performed immunodiagnostic determinations of an immunoreactivity in sera of sepsis and Alzheimer patients which was assignable to the sequence of the first 200 amino acids of LASP-1 confirmed this assumption experimentally in a convincing, impressive manner.

The publications to date on LASP-1 by no means indicate such a possibility. On the basis of the findings available to date, it was not to be expected that the physiological concentrations of LASP-1 in the brain and also in the circulation as a consequence of sepsis and/or brain-specific inflammation, such as Alzheimer's disease, have changed significantly and detectably, and therefore a determination of LASP-1 concentrations in the course of a sepsis process or of an inflammatory brain disease might be of diagnostic interest.

The detection, according to the invention, of comparatively high LASP-1 concentrations in the brain tissue of primates in which an artificial sepsis was induced by toxin administration, together with the simultaneous impossibility of detecting LASP-1 in otherwise completely identically treated samples of control animals, or in other tissue samples of septic animals, and the subsequent immunodiagnostic detection in the human circulation, is highly significant. Since the occurrence was observable only in the treated animals, in particular only a relatively short time after sepsis was induced by toxin administration, it is possible to make use of this fact for providing a promising diagnostic sepsis, infection and inflammation diagnosis method by determination of LASP-1 immunoreactivity. Moreover, the proven suitability of LASP-1 as a diagnostic marker and prognosis marker for Alzheimer's disease is of particular interest.

The determination of LASP-1 can be carried out by any arbitrary suitable assay method, but the determination in a body fluid, including liquor (cerebrospinal fluid) of a patient by an immunodiagnostic route (by means of an immunoassay) using suitable selective antibodies appears most advantageous from practical points of view.

Owing to the fact that, when sepsis is induced experimentally in the brain of primates and subsequently also in the circulation of human patients, an increased occurrence of LASP-1 or of a protein substantially identical thereto could be detected for the first time, the possibility of using the LASP-1 immunoreactivity in particular for diagnostic purposes in association with inflammations and infections which manifest themselves in the brain is thus created. For this purpose, it is possible to prepare LASP-1 or suitable partial peptides thereof or epitopes or epitope combinations specifically by a synthetic or genetic engineering method, optionally also by processes which are now part of the prior art. LASP-1 partial peptides, optionally in marked form, may also be required as calibrators, tracers and competitors for certain assay formats for immunodiagnostic determinations and are prepared for this purpose in the manner explained. Certain currently preferred specific embodiments are described in more detail in the following experimental section.

Furthermore, LASP-1 fragments or suitable partial sequences thereof can be used according to known modern state-of-the-art methods also for producing specific polyclonal or monoclonal antibodies which are suitable as auxiliaries for the diagnostic determination of LASP-1 in body fluids of a patient and/or also as potential therapeutic agents. Certain currently preferred specific polyclonal affinity-purified anti-LASP-1 antibodies are described in more detail in the following experimental section. The production of suitable monoclonal antibodies against known peptide partial sequences is now part of the general prior art and need not be described particularly. Furthermore, antibody production using techniques of direct genetic immunization with a corresponding DNA should also be mentioned expressly. It is therefore within the scope of the present invention to use, for example, a cDNA of LASP-1 or LASP-1 fragments for the immunization, since it has been found in the past that the spectrum of the obtainable antibodies can be extended with the use of such immunization techniques. However, it is also possible to use known antibodies against LASP-1 (cf. for example V. Schreiber et al., Molecular Medicine 4: 675-687, 1998; C. S. Chew et al., Am. J. Physiol. 275 (Cell Physiol. 44): C56-C67, (1998)).

Since, in the course of the work described here, an LASP-1 product which has a molar mass of about 36 kDa and has a solubility sufficient for the determination described was found in the gel of the 2D electrophoresis, it could not be ruled out that the LASP-1 product found is an expression product differing from the actual LASP-1 described in the literature, for example the product of an alternative splicing, and/or has a certain type of glycosylation and/or phosphorylation, which imparts to it the observed solubility and on the basis of which it differs significantly from the 40 kDa product isolated from the stomach wall. It was therefore considered from the start of the investigations as being within the scope of the present invention to carry out the determination of LASP-1 with the aid of a specific assay in which specific partial sequences and/or optionally also glycosylation and/or phosphorylation patterns are detected. The preparation of antibodies, in particular monoclonal antibodies, which recognize specific glycosylations and/or phosphorylations is in principle known and is described, for example, in connection with the determination of certain phosphorylation forms of the so-called tau-proteins as part of the diagnosis of Alzheimer's disease.

In the immunological determination of LASP-1, it is possible in principle to proceed as described, for example, for the selective procalcitonin determination in P. P. Ghillani et al., "Monoclonal antipeptide antibodies as tools to dissect closely related gene products", The Journal of Immunology, Vol. 141, No. 9, 1988, 3156-3163; and P. P. Ghillani et al., "Identification and Measurement of Calcitonin Precursors in Serum of Patients with Malignant Diseases", Cancer Research, Vol. 49, No. 23, 1989, 6845-6851. Variations of the techniques described and/or further immunization techniques can be found by a person skilled in the art in relevant standard works and publications and applied in context.

LASP-1 or optionally LASP-1 fragments or products having a partially identical sequence, such as LAP-1, can, on the basis of the results available, serve as immunoreactivity or specific marker peptides (biomarkers) for the diagnosis and for the monitoring of inflammations and infections (in particular of systemic infections of the sepsis type and inflammations of the brain, such as Alzheimer's disease). Like the determination of procalcitonin, the determination of LASP-1 can be performed for the early differential diagnosis and for the detection and for the preparation of a prognosis, for assessment of the severity and for therapy-accompanying assessment of the course of inflammations and infections, the content of LASP-1 being determined in such a method, preferably in a sample of a biological fluid, including the so-called liquor, or optionally also of a tissue of a patient, and conclusions being drawn about the presence of an inflammation involving the brain or of a sepsis from the determined presence and/or amount of LASP-1, and the result obtained being correlated with the severity of the sepsis and optionally the possibilities of treatment and/or the prospects of treatment being estimated.

A determination of LASP-1 as part of a multiparameter determination in which at least one further inflammation or infection parameter is determined simultaneously and in which a measured result in the form of a set of at least two measured quantities is obtained and is evaluated for the fine diagnosis of the inflammation or infection appears to be of particular interest. Further inflammation or infection parameters of this type are considered to be those which are selected from the group consisting of the parameters which are partly known or are disclosed in the prior or parallel patent applications of the Applicant, which group consists of procalcitonin, CA 125, CA 19-9, S100B, S100A proteins, soluble cytokeratin fragments, in particular CYFRA 21, TPS and/or soluble cytokeratin-1 fragments (sCY1F), the peptides inflammin and CHP, peptide prohormones, glycine N-acyltransferase (GNAT), carbamoyl phosphate synthetase 1 (CPS 1) and the fragments thereof and the C-reactive protein (CRP) or fragments of all said proteins. It is advantageous to carry out the multiparameter determination as a simultaneous determination by means of a chip technology measuring apparatus or an immunochromatographic measuring apparatus, in which the evaluation of the complex measured result obtained using the measuring apparatus is carried out with the aid of a computer program.

In a preferred embodiment, the method is carried out as a heterogeneous sandwich immunoassay in which one of the antibodies is immobilized on an arbitrary solid phase, for example the walls of coated test tubes (for example consisting of polystyrene; "coated tubes"; CT) or on microtitre plates, for example consisting of polystyrene, or on particles, for example magnetic particles, while the other antibody carries a residue which represents a directly detectable label or permits selective linkage with a label and serves for detection of the sandwich structures formed. Delayed or subsequent immobilization using suitable solid phases is also possible.

In principle, it is possible to use all marking techniques which can be used in assays of the type described, including marking with radio isotopes, enzymes or fluorescent, chemoluminescent or bioluminescent labels and directly optically detectable colour markings, such as, for example, gold atoms and stain particles, as used in particular for point-of-care (POC) or accelerated tests. In the case of heterogeneous sandwich immunoassays, the two antibodies may also have parts of a detection system of the type described below in association with homogeneous assays.

It is therefore within the scope of the present invention to design the method according to the invention also as an accelerated test.

The method according to the invention can furthermore be designed as a homogeneous method in which the sandwich complexes formed from the two antibodies and the LASP-1 to be detected remain suspended in the liquid phase. In such a case, it is preferable to mark both antibodies with parts of a detection system, which then permits generation of a signal or triggering of a signal when both antibodies are integrated into a single sandwich. Such techniques can be designed in particular as fluorescence amplification or fluorescence extinction detection methods. A particularly preferred method of this type relates to the use of detection reagents to be employed in pairs, as described, for example, in U.S. Pat. No. 4,822,733, EP-B1-180 492 or EP-B1-539 477 and the prior art cited therein. They permit a measurement which selectively measures only reaction products which contain the two marking components in a single immune complex, directly in the reaction mixture. As an example, reference may be made to the technology offered under the trade names TRACE® (Time Resolved Amplified Cryptate Emission) or KRYPTOR®, which realizes the teachings of the above-mentioned Applications.

Below, the discovery and identification of LASP-1 and the determination thereof in biological fluids (sera or plasmas) of patients suffering from various diseases are described in more detail. The figures show the following:

FIG. 1 Views of 2D electrophoresis gels which permit a comparison of the spot pattern of cytoplasmic brain proteins of a healthy baboon (A) with the brain proteins of a baboon 5 h after a sepsis induced by LPS administration (B). The arrow indicates the positions of the sepsis-specific product according to the invention (LASP-1), which is highlighted by a circle in diagram (B).

Figure 2:
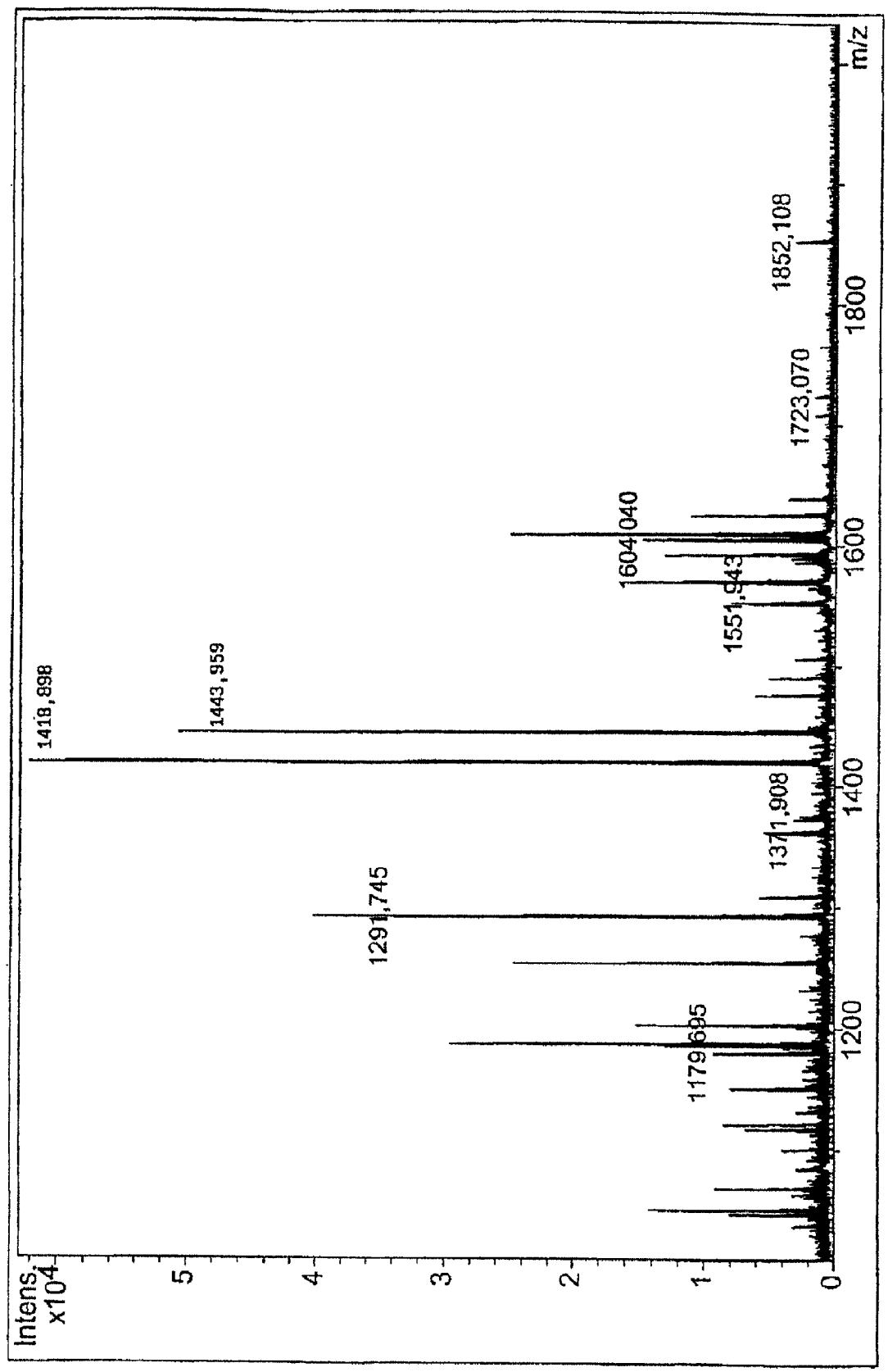

FIG. 2 The mass spectrum of the trypsin-digested product isolated from the gel of the 2D gel electrophoresis.

Figure 3:
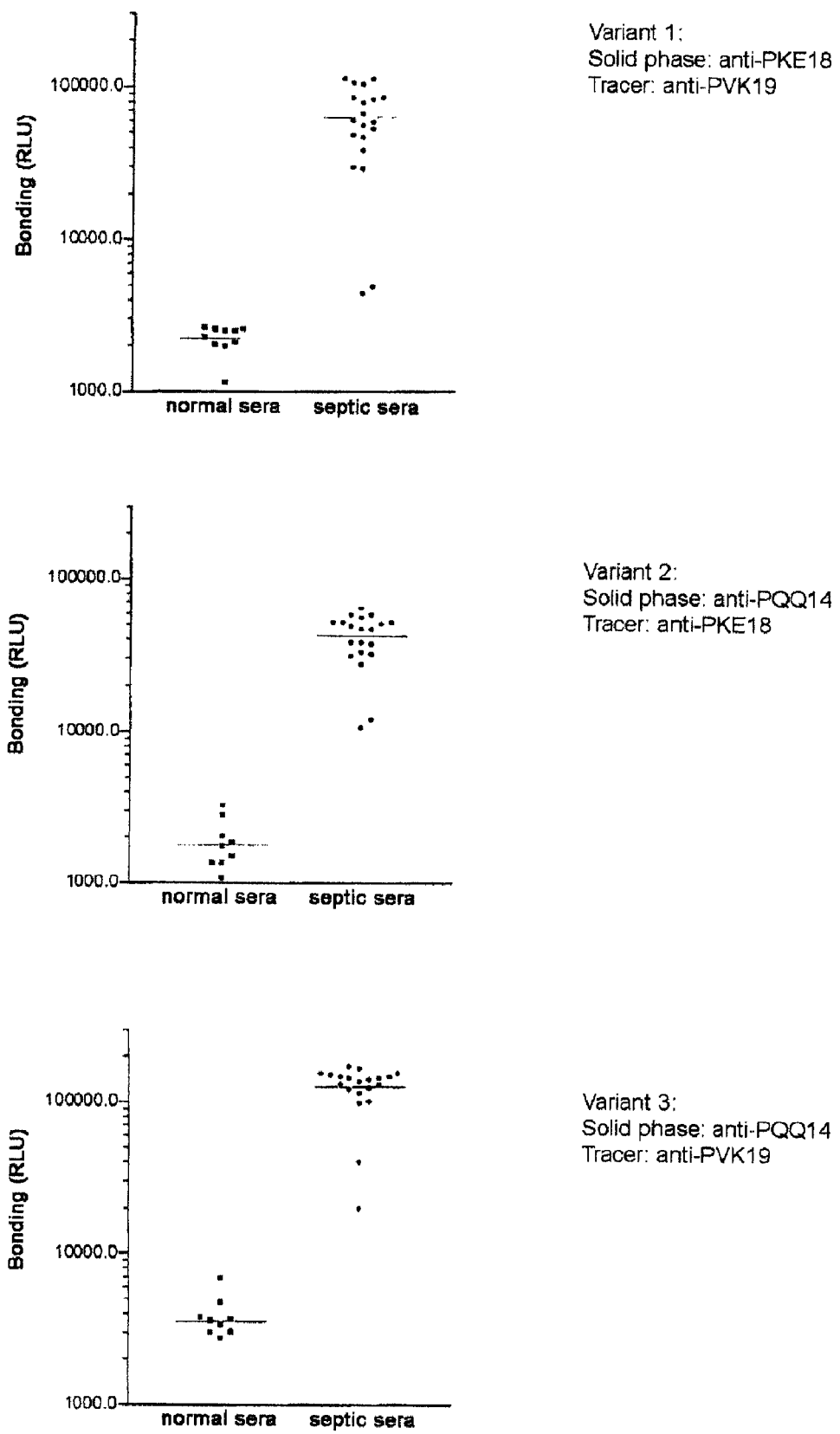

FIG. 3 A comparative representation of the results of the measurement of the LASP-1 (1-200) immunoreactivity using immunoassays with different pairs of three antibodies, which were used in solid phase-bound or marked form and which recognized amino acid sequences 121-137, 147-159 and 170-187 of LASP-1. It can be seen that substantially identical results were obtained with all pairs.

Figure 4:
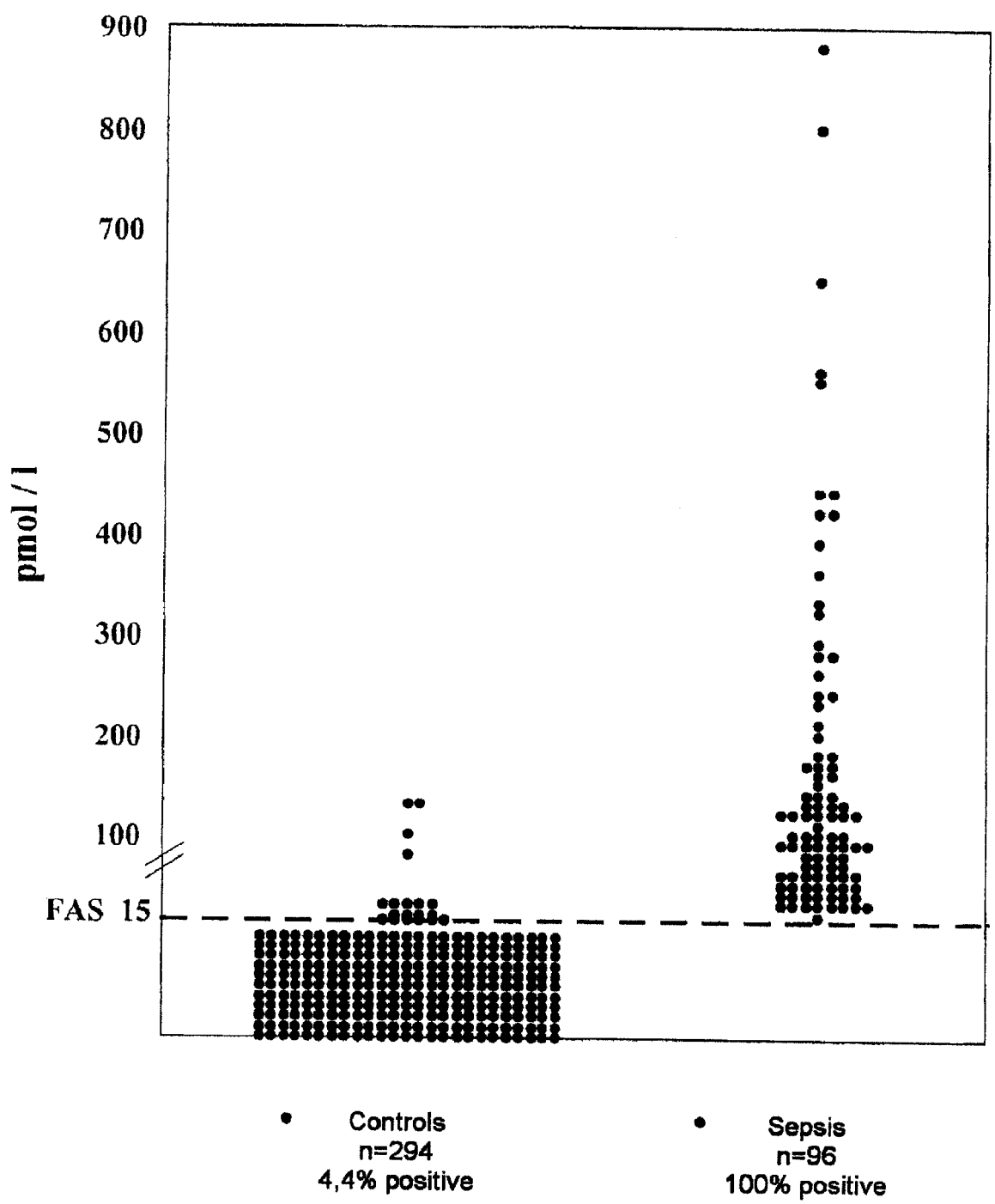

FIG. 4 The results of an immunodiagnostic determination of an LASP-1 (1-200) immunoreactivity in sera of 294 healthy control persons and of 96 patients suffering from sepsis.

Figure 5:
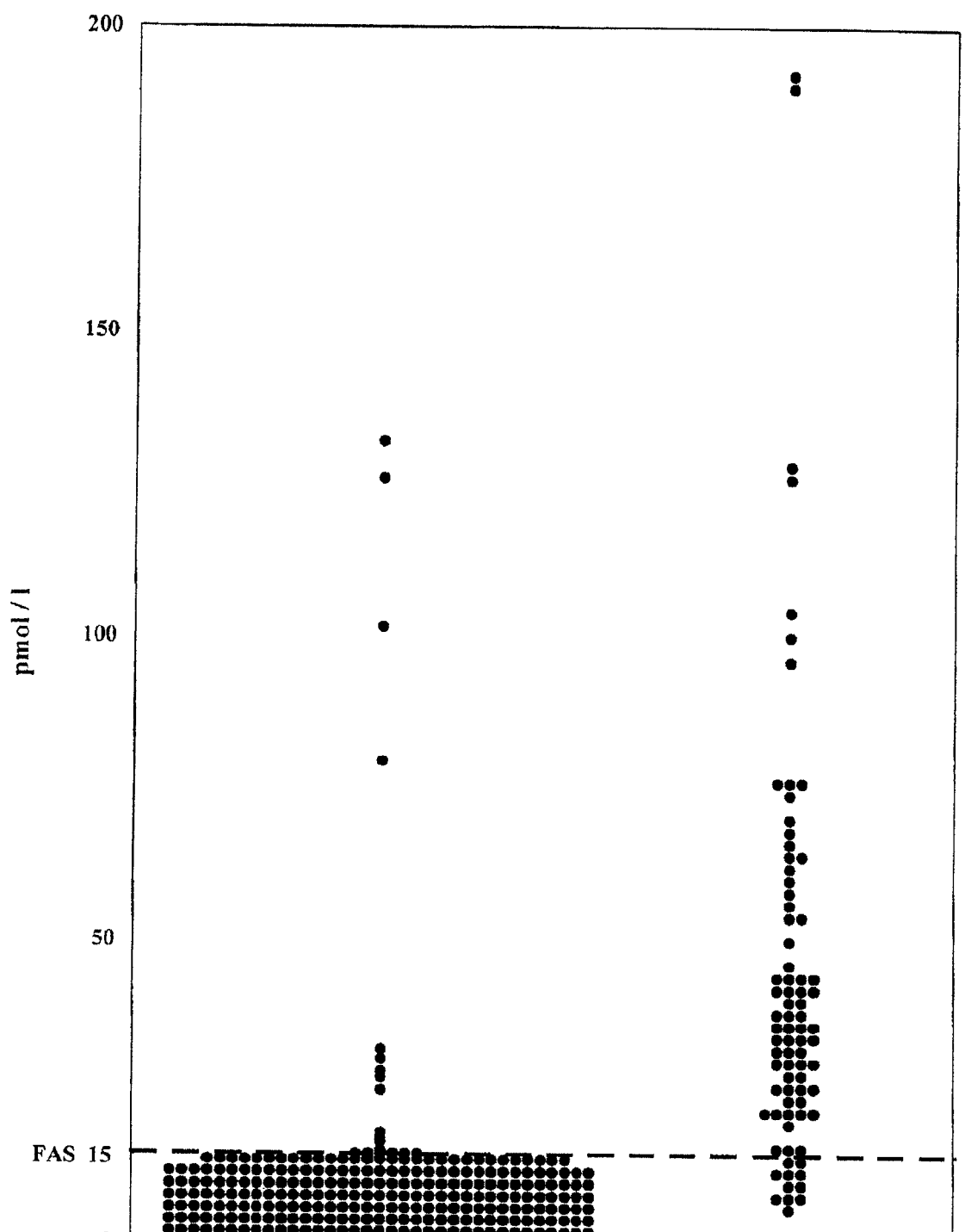

FIG. 5 The results of an immunodiagnostic determination of an LASP-1 (1-200) immunoreactivity in sera of 294 healthy control persons and of 80 patients suffering from Alzheimer's disease.

FIG. 6 The results of an immunodiagnostic determination of an LASP-1 (1-200) immunoreactivity in sera of 294 healthy control persons and of 20 patients suffering from cardiac infarction.

EXPERIMENTAL SECTION

1. Infection Simulation by Endotoxin Administration in an Animal Model (Baboons).

On the basis of the experiments carried out with baboons for the stimulation of procalcitonin secretion by endotoxin injections (cf. H. Redl et al., "Procalcitonin release patterns in a baboon model of trauma and sepsis: Relationship to cytokines and neopterin", Crit Care Med 2000, Vol. 28, No. 11, 3659-3663; H. Redl et al., "Non-Human Primate Models of Sepsis", in: Sepsis 1998; 2:243-253), baboons (male, about 2 years old, weighing from 27 to 29 kg) were each intravenously administered 100 μg of LPS (lipopolysaccharide from Salmonella Typhimurium, source: Sigma) per kg body weight. From 5 to 5.5 h after the injection, the animals were sacrificed by intravenous administration of 10 ml of doletal. Within 60 min of their death, all organs/tissues were dissected and were stabilized by freezing in liquid nitrogen.

During the further processing, 1.5 ml of buffer A (50 mM Tris/HCl, pH 7.1, 100 mM KCl, 20% of glycerol) were added to samples of the individual frozen tissues (1 g) while cooling with nitrogen, and the samples were pulverized in a porcelain mortar to give a powder (cf. J. Klose, "Fractionated Extraction of Total Tissue Proteins from Mouse and Human for 2-D Electrophoresis", in: Methods in Molecular Biology, Vol. 112: 2-D Proteome Analysis Protocols, Humana Press Inc., Totowa, N.J.). After subsequent centrifuging for 1 hour at 100,000 g and +4° C., the supernatant obtained was recovered and was stored at −80° C. until required for further processing.

2. Proteome Analysis Using Cytoplasmic Brain Proteins of Baboons.

Cytoplasmic brain cell protein extracts of, on the one hand, healthy baboons (control) and, on the other hand, baboons which had been injected with LPS were used in a proteome analysis. In the initial analytical 2D gel electrophoresis, brain extract containing 100 μg of protein was stabilized to 9M urea, 70 mM DTT, 2% ampholyte pH 2-4 and then separated by means of analytical 2D gel electrophoresis, as described in J. Klose et al., "Two-dimensional electrophoresis of proteins: An updated protocol and implications for a functional analysis of the genome", Electrophoresis 1995, 16, 1034-1059. The visualization of the proteins in the 2D electrophoresis gel was effected by means of silver staining (cf. J. Heukeshoven et al., "Improved silver staining procedure for fast staining in Phast-System Development Unit. I. Staining of sodium dodecyl gels", Electrophoresis 1988, 9, 28-32).

For evaluation, the protein spot patterns of the samples of treated animals were compared with the protein spot patterns which resulted from brain tissue samples of untreated animals. Furthermore, the protein spot patterns from the brain tissue of treated animals were also compared with those of other tissues of the same treated animals (the results are not shown individually). Substances which occurred in no control sample but additionally in all treated animals were selected for further analytical investigations. FIG. 1 shows a comparison of the 2D electrophoresis gels for a control sample (A) and a sample of a treated animal (B), the additional protein spot in (B) corresponding to a novel protein whose position is highlighted by an arrow and a circle.

The novel specific proteins identified in the protein spot pattern of the analytical 2D gel electrophoresis were then prepared by means of preparative 2D gel electrophoresis using 350 µg of protein (once again cf. (10)). In the preparative 2D gel electrophoresis, the staining was effected by means of Coomassie Brilliant Blue G250 (cf. V. Neuhoff et al., "Improved staining of proteins in polyacrylamide gels including isoelectric focusing gels with clear background at nanogram sensitivity using Coomassie Brilliant Blue G-250 and R-250", Electrophoresis 1988, 9, 255-262).

The protein spots preselected for the further analysis were cut out of the gel, using the method which is described in A. Otto et al., "Identification of human myocardial proteins separated by two-dimensional electrophoresis using an effective sample preparation for mass spectrometry", Electrophoresis 1996, 17, 1643-1650, trypsin-digested and then analyzed by means of mass spectroscopy, in particular with the use of mass spectrometric investigations as described and discussed, for example in G. Neubauer et al., "Mass spectrometry and EST-database searching allows characterization of the multi-protein spliceosome complex", in: nature genetics, vol. 20, 1998, 46-50; J. Lingner et al., "Reverse Transcriptase Motifs in the Catalytic Subunit of Telomerase", in: Science, Vol. 276, 1997, 561-567; M. Mann et al, "Use of mass spectrometry-derived data to annotate nucleotide and protein sequence databases", in: TRENDS in Biochemical Sciences, Vol. 26, 1, 2001, 54-61. The trypsin-digested samples were subjected to MALDI-TOF mass spectrometry.

3. Identification of LASP-1

As shown in FIGS. 1(A) and 1(B), brain tissue extracts of baboons to which an LPS injection had been administered contain, inter alia, a spot of a protein for which a molecular weight of approx. 36 kDa±3 kDa was estimated on the basis of the gel electrophoresis data in comparison with marker substances of known molecular weight, while an isoelectric point of approx. 6.6-7.0 was determined from the relative position of the protein from the first dimension.

In the mass analysis of the trypsin digestion of the novel protein spot, an attempt at assignment to peptides was undertaken for 21 fragments on the basis of database information. The result was that twelve of the assignments obtained corresponded to fragments of the protein chain of the phosphoprotein LASP-1 (SEQ ID NO:1). The so-called "sequence coverage" was 38%, which, according to the recognized criteria customary in the field, is to be regarded as unambiguous identification of the protein contained in the spot as the protein chain of LASP-1.

Thus, for example, it was possible to assign the following mass fragments to the LASP-1 protein chain (SEQ ID NO:1): 1202.714; 1254.615; 1291.745; 1360.813; 1418.898; 1443.959; 1489.826; 1551.943; 1604.040; 1608.960; in particular, the assignment according to MS-Fit 3.3.1. Protein Prospector 3.4.1., Database NCBIno. 7.25.2002 was as follows:

The mass 1202.714 (MH+) corresponds to the sequence QQSELQSQVR (SEQ ID NO:2). The theoretical molecular weight of this fragment is 1201.604. In the amino acid sequence of LASP-1, this sequence occurs at the positions 76-95.

The mass 1254.615 corresponds to the sequence ACFHCETCK (SEQ ID NO:3). The theoretical molecular weight of this fragment is 1253.498. In the amino acid sequence of LASP-1, this sequence occurs at the positions 28-36.

The mass 1291.745 corresponds to the sequence KPYCNAHYPK (SEQ ID NO:4). The theoretical molecular weight of this fragment is 1290.617. In the amino acid sequence of LASP-1, this sequence occurs at the positions 50-59.

The mass 1360.813 corresponds to the sequence VNCLDKFWHK (SEQ ID NO:5). The theoretical molecular weight of this fragment is 1359.675. In the amino acid sequence of LASP-1, this sequence occurs at the positions 18-27.

The mass 1418.898 corresponds to the sequence GFSVVADTPELQR (SEQ ID NO:6). The theoretical molecular weight of this fragment is 1417.719. In the amino acid sequence of LASP-1, this sequence occurs at the positions 97-109.

The mass 1443.959 corresponds to the sequence LKQQSELQSQVR (SEQ ID NO:7). The theoretical molecular weight of this fragment is 1442.783. In the amino acid sequence of LASP-1, this sequence occurs at the positions 74-85.

The mass 1489.826 corresponds to the sequence MGPSGGEGMEPERR (SEQ ID NO:8). The theoretical molecular weight of this fragment is 1488.644. In the amino acid sequence of LASP-1, this sequence occurs at the positions 131-144.

The mass 1551.943 was assigned to the sequence TGDTGMLPANYVEAI (SEQ ID NO:9). The theoretical molecular weight of this fragment is 1550.728. In the amino acid sequence of LASP-1, this sequence occurs at the positions 247-261.

The mass 1604.040 corresponds to the sequence GKGFSVWADTPELQR (SEQ ID NO:10). The theoretical molecular weight of this fragment is 1602.836. In the amino acid sequence of LASP-1, this sequence occurs at the positions 95-109.

The mass 1608.960 corresponds to the sequence QSFTMVADTPENLR (SEQ ID NO:11). The theoretical molecular weight of this fragment is 1607.761. In the amino acid sequence of LASP-1, this sequence occurs at the positions 60-73.

Nine of the ten identified fragments described occur in the segment of the amino acids 1-200 of LASP-1, i.e. that protein segment which is present before the so-called SH3 domain, which begins at amino acid 202.

According to recognized principles of interpretation, such an agreement is considered to be a safe identification of the product from the protein spot as a protein corresponding to LASP-1 at least in the range of the amino acids 1-200. The molecular weight of unphosphorylated LASP-1 (261 amino acids; cf. SEQ ID NO:1) is, however, only 29,717 Dalton. However, it is known from the literature that, in molar mass determinations by gel electrophoresis, LASP-1 appears to exhibit irregular behaviour so that the deviations found for molar masses are not necessarily in contradiction to the identification of the substance found as LASP-1 with the amino acid sequence according to SEQ ID NO:1.

Equally, however, it cannot be completely ruled out that the product detected differs from said LASP-1, for example is the product of an alternative splicing. In order to explore the possibility that it could have been another related expression product, a subsequent investigation was therefore carried out with the intention of exploring the possibility of assignment of the protein spot found to a closely related longer protein. Subsequent investigations carried out using information implicitly present in cDNA databases led to the discovery of a longer protein which is related to LASP-1 and is likely to be the product of an alternative splicing and, instead of the SH3 domain, has an alternative C-terminal amino acid residue of 123 amino acids. The protein has the same amino acids 1-200

LASP-1, so that an immunoreactivity comparable with LASP-1 was to be expected. Said related protein was assigned the name LAP-1. Regarding its identification, further information is to be found in the following section 5.

4. Immunodiagnostic Determination of LASP-1 Immunoreactivities in Sera of Human Patients 4.1. Immoassays—Material and Methods 4.1.1. Peptide Syntheses Three ranges were selected (Pos. 121-137: peptide range 1; Pos. 147-159: peptide range 2; Pos. 170-187: peptide range 3), derived from the known amino acid sequence of human LASP-1. In each case supplemented by an N-terminal cysteine residue, the ranges were chemically synthesized as soluble peptides by standard methods, purified, subjected to quality control by means of mass spectrometry and reversed phase HPLC and lyophilized in aliquots (JERINI AG, Berlin, Germany). The amino acid sequences of the synthetic peptides are:

```
Peptide PKE18    CKYHEEFEKSRMGPSGGE    (SEQ ID NO: 13)

Peptide PPQ14    CQDGSSYRRPLEQQ        (SEQ ID NO: 14)

Peptide PVK19    CVYQQPQQQPVAQSYGGYK   (SEQ ID NO: 17)
```

As standard peptides, the following peptide which was composed of the positions 121-137, 147-159, 170-187 of LASP-1 according to SEQ ID NO:1 was also synthesized:

```
PeptidePKK5 4
                                      (SEQ ID NO: 15)
KYHEEFEKSRMGPSGGEGGGQDGSSYRRPLEQQGGG-VYQQPQQQPVAQS

YGGYK
```

The following considerations were critical for the choice of peptides:

The protein LASP-1 comprising 261 amino acids contains two potential protein binding domains, the LIM domain at the N-terminus (Pos. 5-56) and the SH3 domain at the C-terminus (Pos. 202-261) (cf. Tomasetto et al., loc. cit. 1995). Whether and which protein bindings LASP-1 enters into via these domains is unknown to date. Two possible actin-binding domains are described as further structural features of LASP-1: these are located directly in succession in the range of Pos. 61-133 (Schreiber et al., loc. cit. 1998), and it has been shown that LASP-1 can actually bind actin (Schreiber et al., loc. cit. 1998). The binding to actin is influenced by phosphorylation at the positions 99 and 146 (Chew et al. loc. cit., 2002).

For the development of immunoassays for LASP-1 and for examining the question as to whether LASP-1 is also detectable extracellularly, i.e. as immunoreactivity in normal and pathological human serum/plasma samples, the inventors made use of the known information described above for the structure of LASP-1: three peptides which do not lie in the range of the LIM and SH3 domains were selected for the immunization, since these domains in LASP-1 might not have been accessible to antibodies owing to bound protein. Furthermore, the three selected proteins do not contain the phosphorylation sites described. For one of the peptides, it was accepted that it is partly in a possible actin-binding range.

4.1.2. Conjugation and Immunization

By means of MBS (m-maleimidobenzoyl-N-hydroxysuccinimide ester), the peptides PKE18, PPQ14 and PVK19 were each conjugated with the carrier protein KLH (keyhole limpet hemocyanine) (cf. working instructions "NHS-esters-maleimide crosslinkers" from PIERCE, Rockford, Ill., USA). Sheep were immunized with these conjugates according to the following scheme: each sheep initially received 100 µg of conjugate (stated mass based on the peptide content of the conjugate) and then 50 µg of conjugate every 4 weeks (stated mass based on the peptide content of the conjugate). Beginning with the fourth month after the beginning of the immunization, 700 ml of blood per sheep were taken every 4 weeks and antiserum was obtained therefrom by centrifuging. Conjugations, immunizations and recovery of antisera were carried out by MicroPharm, Carmarthenshire, UK.

4.1.3. Purification of the Antibodies

In a 1-step method, the peptide-specific antibodies were prepared from the antisera which had been obtained beginning with the fourth month after immunization.

For this purpose, the peptides PKE18, PQQ14 and PVK19 were first coupled to SulfoLink Gel (cf. working instructions "SulfoLink Kit" from PIERCE, Rockford, Ill., USA). 5 mg of peptide per 5 ml of gel were offered for coupling.

The affinity purification of peptide-specific antibodies from sheep antisera against both peptides was carried out as follows:

The peptide columns were first washed three times alternately with 10 ml each of elution buffer (50 mM citric acid, pH 2.2) and binding buffer (100 mm sodium phosphate, 0.1% Tween, pH 6.8). 50 ml of the antisera were filtered over 0.2 µm, and the column material present was added. For this purpose, the gel was rinsed quantitatively with 10 ml of binding buffer from the column. The incubation was effected overnight at room temperature with swirling. The batches were transferred quantitatively into empty columns (NAP 25, Pharmacia, emptied). The run-throughs were discarded. The material was then washed protein-free (protein content of the wash eluate <0.02 A280 nm) with 250 ml of binding buffer. Elution buffer was added to the washed columns, and 1 ml fractions were collected. The protein content of each fraction was determined by means of the BCA method (cf. working instructions from PIERCE, Rockford, Ill., USA). Fractions having protein concentrations of >0.8 mg/ml were pooled, neutralized with PBS buffer and thus diluted to protein concentrations of about 1 mg/ml. The yields were: 45 mg of anti-PKE18 antibody, 59 mg of anti-PQQ14 antibody and 14 mg of anti-PVK19 antibody.

4.1.4. Marking

For the chemiluminescent marking of the antibodies, 10 µl portions of MA70 acridinium NHS ester (1 mg/ml; from HOECHST Behring) were added to 100 ml of the anti-PVK19 antibody (1 mg/ml) and 125 µl of the anti-PQQ14 antibody (0.8 mg/ml) and incubated for 15 minutes at room temperature. Thereafter, 400 µl of 1 M glycine were added in each case and incubation was effected for a further 10 minutes. Thereafter, the marking batches were subjected to a buffer change using NAP-5 gel filtration columns (Pharmacia) in 1 ml each of mobile phase A (50 mM potassium phosphate, 100 mM NaCl, pH 7.4) according to the working instructions and thereby freed from low molecular weight components. For separating off final residues of labels not bound to antibodies, gel filtration HPLCs were carried out (column: Waters Protein Pak SW300). The samples were applied and were chromatographed at a flow rate of 1 ml/min using mobile phase A. The wavelengths 280 nm and 368 nm were measured using a flow-through photometer. The absorption ratio 368 nm/280 nm as a measure of the degree of marking of the antibodies was 0.10 for both antibodies. The monomeric fractions containing antibodies (retention time 8-10 min) were collected, and were collected in 3 ml of 100 mM sodium phosphate, 150 mM NaCl, 5% bovine serum albumin, 0.1% sodium azide, pH 7.4.

4.1.5. Coupling

Irradiated 5 ml polystyrene tubes (from Greiner) were coated with anti-PQQ14 antibodies or anti-PKE18 antibodies, as follows: the antibodies were diluted to a concentration of 6.6 µg/ml in 50 mM Tris, 100 mM NaCl, pH 7.8. 300 µl of this solution were pipetted into each tube. The tubes were incubated for 20 hours at 22° C. The solution was filtered with suction. Each tube was then filled with 4.2 ml of 10 mM sodium phosphate, 2% Karion FP, 0.3% bovine serum albumin, pH 6.5. After 20 hours, the solution was filtered with suction. Finally, the tubes were dried in a vacuum dryer.

4.2. Carrying Out the Immoassays and Evaluation Thereof

4.2.1. Assay Design and Procedure

An assay buffer having the following composition was prepared:

100 mM sodium phosphate, 150 mM NaCl, 5% bovine serum albumin, 0.1% unspecific sheep IgG, 0.1% sodium azide, pH 7.4

A chemically synthesized artificial peptide PKK54, which contains Pos. 121-137, 147-159, 170-187 of LASP-1 (SEQ ID NO:15), served as standard material. This peptide was diluted serially in normal horse serum (from SIGMA). The standards thus prepared were assigned concentrations according to the amount of peptide weighed in.

Measurement samples were EDTA plasmas or sera from apparently healthy persons, from patients suffering from sepsis, from patients suffering from Alzheimer's disease and from patients suffering from cardiac infarction.

Three types of sandwich assays were carried out. The following antibody combinations were used:
Tube: anti-PKE18/tracer: anti-PVK19
Tube: anti-PQQ14/tracer: anti-PKE18
Tube: anti-PQQ14/tracer: anti-PVK19

All assays were carried out as follows:

50 µl each of standard or sample and 150 µl of assay buffer were pipetted into the test tubes. Incubation was effected for two hours at 22° C. with shaking. Washing was then effected 4 times with 1 ml of wash solution (0.1% Tween 20) per tube each time. 200 µl of assay buffer, containing 0.5 million RLU of the MA70-marked tracer antibody, were then pipetted into each tube. Incubation was effected for two hours at 22° C. with shaking. Washing was then effected 4 times with 1 ml of wash solution (0.1% Tween 20) per tube each time, the tube was allowed to drip off and the chemiluminescence bound to the tube measured in a luminometer (from BERTHOLD, LB952T; base reagents BRAHMS AG).

Using the MultiCalc software (spline fit), the concentration of LASP-1 immunoreactivity was read.

4.2.2. Results

Surprisingly, it was found that, with all three sandwich assays described above, a substantial and comparable LASP-1 immunoreactivity was detectable in sera of patients suffering from sepsis (cf. FIG. 3). This immunoreactivity was substantially higher than in the case of control samples from healthy persons. The detected occurrence of LASP-1 immunoreactivity in the blood circulation was surprising against the background of knowledge about LASP-1, since LASP-1 contains no structural features (such as a signal sequence) which would make it possible to predict extracellular localization of the molecule. The prior art, too, provides no indication at all of such possible localization. Rather, intracellular localization in cell membrane extensions is described (Schreiber et al., loc. cit. 1998).

With one of the assays (tube: anti-PQQ14/tracer: anti-PVK19), more extensive measurements were carried out. Dilutions of standard peptide PKK54 in horse serum served for standardization. The substantial increase of LASP-1 immunoreactivity in a larger number of cases of sera from patients suffering from sepsis (FIG. 4) was confirmed. An immunoreactivity likewise increased compared with healthy controls was also detected for patients suffering from Alzheimer's disease (FIG. 5) and, to a somewhat lesser extent, for patients suffering from cardiac infarction (FIG. 6).

4.2.3. Information on Protein Binding of LASP-1 in Serum

The signal intensities for the individual serum samples—approximately proportional to the analyte concentration in the sandwich immunoassay—correlated between three different assays (FIG. 3). This correlation shows that all three epitopes are accessible in a similar manner for the binding of the antibodies used in all measured samples. For an analyte which is not bound to other proteins, this would be expected and not surprising. For LASP-1, however, several possibilities have been described for binding to proteins (loc. cit.). One of the epitopes (Pos. 121-137) overlaps with an actin binding site. Evidently, this binding site is therefore not occupied with LASP-1 immunoreactivity in the analyte measurable in this serum. The other two epitopes (Pos. 147-159 and Pos. 170-187) are outside protein binding domains (actin-binding sites, LIM, SH3). A direct influence on antibody binding at these isotopes by bound proteins is therefore not to be expected. However, the possibility of the occurrence of indirect steric hindrance of the antibody binding in the case of protein binding cannot be ruled out. However, this is evidently not the case. Whether the LASP-1 immunoreactivity in the serum is actually freely present has not yet been proved by the present analyses and may have to be determined by further investigations.

5. Identity of the LASP-1 Immunoreactivity in Serum

A comparison of the amino acid sequences of the three peptides PKE18 (Pos. 121-137 in LASP-1; SEQ ID NO:13), PQQ14 (Pos. 147-159 in LASP-1; SEQ ID NO:14) and PVK19 (Pos. 170-187 in LASP-1; SEQ ID NO:17) used for producing the anti-LASP-1 antibodies with the sequences entered in the GenBank database for all known human proteins or proteins derived from cDNAs showed that, in addition to LASP-1 (e.g. Accession No. BC012460), a second protein which contains these sequences exists (Accession No. BC007560). This is referred to below as LAP-1. It can be assigned the sequence according to SEQ ID NO:16. The immunoreactivity measured by the immunoassays described above could therefore originate both from LASP-1 (SEQ ID NO:1) itself and from LAP-1 (SEQ ID NO:16).

The Applicant has not become aware of any prior art relating to LAP-1 over and above the entries on the primary structure in the database. In order to obtain more detailed information on the structure and genesis of LASP-1 in comparison with LAP-1, the inventors themselves therefore carried out more extensive analyses, the results of which are summarized below:

LASP-1 and LAP-1 evidently result from different splicing of the primary transcript of one and the same gene: the sequences of the cDNAs of LASP-1 and LAP-1 (Accession No. BC007560 and BC012460) were compared with the sequence of the human genome. An associated gene was localized at chromosome 17, close to 17q21, region 39.023K-39.076K. By comparison of the sequences, it was possible to derive an exon-intron structure of the gene. The cDNAs for LASP-1 and LAP-1 result from the splicing of eight exons. Exons 2-5 do not differ for the two cDNAs. However, exons 6, 7 and 8 are not identical in the two cDNAs but overlap one another. Exon 1 differs in the two cDNAs with regard to the length at the 5' terminus. What remains unclear is whether the different lengths of exon 1 of the two cDNAs result from different transcription initiations or from different breaks in the reverse transcription of the mRNAs. The translated region extends for both cDNAs from the 3' region into the 5'-region of exon 7: the amino acid sequences of the two translation products are identical up to the amino acid proline (Pos. 200), but completely different thereafter (cf. SEQ ID NO:1 in comparison with SEQ ID NO:16). LASP-1 comprises 261 amino acids altogether, and LAP-1 comprises 323 amino acids. In LASP-1, the SH3 domain begins at position 202. It is precisely this SH3 region which is not present in LAP-1 but is replaced by another region of unknown function. The lack of the SH3 domain in LAP-1 led to its naming (in "LASP-1", S represents SH3 domain).

Both for LASP-1 and for LAP-1, ESTs (expressed sequence tags) are present in the relevant GenBank "Human EST entries" database (e.g. BU553748 for LASP-1 and BG281978 for LAP-1). This clearly shows that the entries described above, BC007560 and BC012460, are not singular observations or even artifacts but rather indicate that both splicing variants are actually expressed. However, the conditions under which the gene is expressed in LASP-1 or LAP-1 are unknown.

On the basis of the substantial sequence identity with LASP-1, a determination and/or codetermination of LAP-1 is also to be regarded as a determination according to the present invention.

If, for an assay method, the reagents are chosen so that the assay is capable of distinguishing between LASP-1 and LAP-1, for example by choosing the binding partners (solid phase-bound or marked) in a sandwich assay in such a way that at least one of them specifically recognizes an epitope in the C-terminal part above position 200 of LAP-1 or LASP-1, in particular above position 200 of LAP-1, it is possible to check whether the LASP-1 immunoreactivity detected in a biological fluid is completely or partly attributable to LAP-1, and LAP-1 can also be determined alone alongside LASP-1, or alongside the total amount of LASP-1 and LAP-1, and the clinical relevance of the presence of LAP-1 for sepsis and/or Alzheimer's disease can thus be explored more exactly.

Therapeutic Potential of the Novel Discoveries

The function of the greatly increased LASP-1 immunoreactivity observed under pathological conditions in the blood circulation is unclear. However, simply the circumstance that an increase is associated with a pathological state suggests that the LASP-1 immunoreactivity is involved in the molecular mechanism of the disease or in the endogenous attempt to fight the disease, and possibly even plays a key role thereby. It is therefore promising to carry out further investigations based on the discoveries in the present Application and with a therapeutic objective. Depending on whether the LASP-1 immunoreactivity tends to be harmful or useful, therapeutic benefits will arise either through an exogenous reduction or increase in the LASP-1 immunoreactivity.

The increased LASP-1 or possibly LAP-1 concentrations found for the first time permit their use as novel biomarkers for sepsis and inflammations, in particular infectious inflammations, and Alzheimer's disease and also in association with cardiac diseases, in particular in cardiac infarction and other severe cardiovascular diseases and provisionally also in cancer. The occurrence of LASP-1 during the disease in the circulation of patients suffering from sepsis, Alzheimer's disease and cardiac infarction, which has been proved for the first time, furthermore opens up novel interesting research aspects for the therapy of the relevant diseases.

The invention claimed is:

1. A method for diagnosing Alzheimer's disease in a patient suspected of having Alzheimer's disease, the method comprising:
   a) determining the concentration of LIM and SH3 Domain Protein-1 (LASP-1) in a blood or serum sample from said patient; and
   b) comparing said concentrations to the corresponding concentration in a healthy control sample, wherein an elevated concentration of LASP-1 protein in the sample from the patient suspected of having Alzheimer's disease is indicative of Alzheimer's disease.

2. The method of claim 1, wherein the concentration of LASP-1 protein is determined by an immunodiagnostic assay of the sandwich type.

3. The method of claim 2, wherein the LASP-1 determined is the LASP-1 protein from amino acid positions 121-187 of SEQ ID NO: 1.

4. The method of claim 2, wherein the immunodiagnostic assay employs a pair of antibodies, wherein one of the antibodies of the pair is raised against a peptide comprising the amino acid sequence of SEQ ID NO:13 and the other antibody of the pair is raised against a peptide comprising the amino acid sequence of SEQ ID NO: 17.

5. The method of claim 3, wherein the LASP-1 protein is in a posttranslational soluble form.

6. The method of claim 5, wherein the protein is glycosylated.

7. The method of claim 5, wherein the protein is phosphorylated.

* * * * *

UNITED STATES PATENT AND TRADEMARK OFFICE
CERTIFICATE OF CORRECTION

PATENT NO. : 7,763,435 B2  
APPLICATION NO. : 12/041370  
DATED : July 27, 2010  
INVENTOR(S) : Andreas Bergmann et al.

Page 1 of 1

It is certified that error appears in the above-identified patent and that said Letters Patent is hereby corrected as shown below:

Title Page item 73

Delete "B.R.A.H.M.S." and insert --B.R.A.H.M.S--

Signed and Sealed this

Ninth Day of November, 2010

David J. Kappos
*Director of the United States Patent and Trademark Office*

SEQUENCE LISTING

<160> NUMBER OF SEQ ID NOS: 17

<210> SEQ ID NO 1
<211> LENGTH: 261
<212> TYPE: PRT
<213> ORGANISM: Homo sapiens

<400> SEQUENCE: 1

```
Met Asn Pro Asn Cys Ala Arg Cys Gly Lys Ile Val Tyr Pro Thr Glu
 1               5                  10                  15

Lys Val Asn Cys Leu Asp Lys Phe Trp His Lys Ala Cys Phe His Cys
            20                  25                  30

Glu Thr Cys Lys Met Thr Leu Asn Met Lys Asn Tyr Lys Gly Tyr Glu
        35                  40                  45

Lys Lys Pro Tyr Cys Asn Ala His Tyr Pro Lys Gln Ser Phe Thr Met
    50                  55                  60

Val Ala Asp Thr Pro Glu Asn Leu Arg Leu Lys Gln Gln Ser Glu Leu
65                  70                  75                  80

Gln Ser Gln Val Arg Tyr Lys Glu Glu Phe Glu Lys Asn Lys Gly Lys
                85                  90                  95

Gly Phe Ser Val Val Ala Asp Thr Pro Glu Leu Gln Arg Ile Lys Lys
            100                 105                 110

Thr Gln Asp Gln Ile Ser Asn Ile Lys Tyr His Glu Glu Phe Glu Lys
```

-continued

```
                115                 120                 125
Ser Arg Met Gly Pro Ser Gly Glu Gly Met Glu Pro Glu Arg Arg
    130                 135                 140
Asp Ser Gln Asp Gly Ser Ser Tyr Arg Pro Leu Glu Gln Gln Gln
145                 150                 155                 160
Pro His His Ile Pro Thr Ser Ala Pro Val Tyr Gln Gln Pro Gln
                165                 170                 175
Gln Pro Val Ala Gln Ser Tyr Gly Gly Tyr Lys Glu Pro Ala Ala Pro
        180                 185                 190
Val Ser Ile Gln Arg Ser Ala Pro Gly Gly Gly Lys Arg Tyr Arg
    195                 200                 205
Ala Val Tyr Asp Tyr Ser Ala Ala Asp Glu Asp Glu Val Ser Phe Gln
    210                 215                 220
Asp Gly Asp Thr Ile Val Asn Val Gln Gln Ile Asp Asp Gly Trp Met
225                 230                 235                 240
Tyr Gly Thr Val Glu Arg Thr Gly Asp Thr Gly Met Leu Pro Ala Asn
                245                 250                 255
Tyr Val Glu Ala Ile
        260

<210> SEQ ID NO 2
<211> LENGTH: 10
<212> TYPE: PRT
<213> ORGANISM: Homo sapiens

<400> SEQUENCE: 2

Gln Gln Ser Glu Leu Gln Ser Gln Val Arg
1               5                   10

<210> SEQ ID NO 3
<211> LENGTH: 9
<212> TYPE: PRT
<213> ORGANISM: Homo sapiens

<400> SEQUENCE: 3

Ala Cys Phe His Cys Glu Thr Cys Lys
1               5

<210> SEQ ID NO 4
<211> LENGTH: 10
<212> TYPE: PRT
<213> ORGANISM: Homo sapiens

<400> SEQUENCE: 4

Lys Pro Tyr Cys Asn Ala His Tyr Pro Lys
1               5                   10

<210> SEQ ID NO 5
<211> LENGTH: 10
<212> TYPE: PRT
<213> ORGANISM: Homo sapiens

<400> SEQUENCE: 5

Val Asn Cys Leu Asp Lys Phe Trp His Lys
1               5                   10

<210> SEQ ID NO 6
<211> LENGTH: 13
<212> TYPE: PRT
<213> ORGANISM: Homo sapiens
```

```
<400> SEQUENCE: 6

Gly Phe Ser Val Val Ala Asp Thr Pro Glu Leu Gln Arg
 1               5                  10

<210> SEQ ID NO 7
<211> LENGTH: 12
<212> TYPE: PRT
<213> ORGANISM: Homo sapiens

<400> SEQUENCE: 7

Leu Lys Gln Gln Ser Glu Leu Gln Ser Gln Val Arg
 1               5                  10

<210> SEQ ID NO 8
<211> LENGTH: 14
<212> TYPE: PRT
<213> ORGANISM: Homo sapiens

<400> SEQUENCE: 8

Met Gly Pro Ser Gly Gly Glu Gly Met Glu Pro Glu Arg Arg
 1               5                  10

<210> SEQ ID NO 9
<211> LENGTH: 15
<212> TYPE: PRT
<213> ORGANISM: Homo sapiens

<400> SEQUENCE: 9

Thr Gly Asp Thr Gly Met Leu Pro Ala Asn Tyr Val Glu Ala Ile
 1               5                  10                  15

<210> SEQ ID NO 10
<211> LENGTH: 15
<212> TYPE: PRT
<213> ORGANISM: Homo sapiens

<400> SEQUENCE: 10

Gly Lys Gly Phe Ser Val Val Ala Asp Thr Pro Glu Leu Gln Arg
 1               5                  10                  15

<210> SEQ ID NO 11
<211> LENGTH: 14
<212> TYPE: PRT
<213> ORGANISM: Homo sapiens

<400> SEQUENCE: 11

Gln Ser Phe Thr Met Val Ala Asp Thr Pro Glu Asn Leu Arg
 1               5                  10

<210> SEQ ID NO 12

<400> SEQUENCE: 12

000

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Lys Tyr His Glu Glu Phe Glu Lys Ser Arg Met Gly Pro Ser Gly
```

```
             1               5                  10                  15
Gly Glu

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Gln Asp Gly Ser Ser Tyr Arg Arg Pro Leu Glu Gln Gln
 1               5                  10

<210> SEQ ID NO 15
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Tyr His Glu Glu Phe Glu Lys Ser Arg Met Gly Pro Ser Gly Gly
 1               5                  10                  15

Glu Gly Gly Gly Gln Asp Gly Ser Ser Tyr Arg Arg Pro Leu Glu Gln
             20                  25                  30

Gln Gly Gly Gly Val Tyr Gln Gln Pro Gln Gln Pro Val Ala Gln
         35                  40                  45

Ser Tyr Gly Gly Tyr Lys
     50

<210> SEQ ID NO 16
<211> LENGTH: 323
<212> TYPE: PRT
<213> ORGANISM: Homo sapiens

<400> SEQUENCE: 16

Met Asn Pro Asn Cys Ala Arg Cys Gly Lys Ile Val Tyr Pro Thr Glu
 1               5                  10                  15

Lys Val Asn Cys Leu Asp Lys Phe Trp His Lys Ala Cys Phe His Cys
             20                  25                  30

Glu Thr Cys Lys Met Thr Leu Asn Met Lys Asn Tyr Lys Gly Tyr Glu
         35                  40                  45

Lys Lys Pro Tyr Cys Asn Ala His Tyr Pro Lys Gln Ser Phe Thr Met
     50                  55                  60

Val Ala Asp Thr Pro Glu Asn Leu Arg Leu Lys Gln Gln Ser Glu Leu
 65                  70                  75                  80

Gln Ser Gln Val Arg Tyr Lys Glu Glu Phe Glu Lys Asn Lys Gly Lys
                 85                  90                  95

Gly Phe Ser Val Val Ala Asp Thr Pro Glu Leu Gln Arg Ile Lys Lys
            100                 105                 110

Thr Gln Asp Gln Ile Ser Asn Ile Lys Tyr His Glu Glu Phe Glu Lys
        115                 120                 125

Ser Arg Met Gly Pro Ser Gly Gly Glu Gly Met Glu Pro Glu Arg Arg
    130                 135                 140

Asp Ser Gln Asp Gly Ser Ser Tyr Arg Arg Pro Leu Glu Gln Gln Gln
145                 150                 155                 160
```

```
Pro His His Ile Pro Thr Ser Ala Pro Val Tyr Gln Gln Pro Gln Gln
            165                 170                 175

Gln Pro Val Ala Gln Ser Tyr Gly Gly Tyr Lys Glu Pro Ala Ala Pro
            180                 185                 190

Val Ser Ile Gln Arg Ser Ala Pro Ile Cys Leu Gln His Ile Pro Arg
            195                 200                 205

His Arg Ile Arg Pro Gly Arg Asp Pro Ser Ile Leu Gln Cys Leu Cys
            210                 215                 220

Phe Leu Lys Pro Ala Thr Ala Cys Asp Ser Tyr Pro Ser Ser Ser Phe
225             230                 235                 240

Phe Cys Gln Leu Lys Pro Ser Ser Ala Thr Ser Ala Gly Ser Leu Leu
            245                 250                 255

Trp Gln Ala Ser Pro Leu Ile Asp Phe Leu Val Phe Ser Leu Asp Gly
            260                 265                 270

Thr Gly Met Gly Leu Ser Gly Gly Gly Arg Gly Pro Trp Gly Arg Ala
            275                 280                 285

Gly Met Gly Asp Leu Leu Ala Cys Gly Pro His Leu Pro Leu Cys Ser
            290                 295                 300

Leu Pro Ser His Pro Pro Ala Gln Leu Leu Thr Tyr Pro His Ile Pro
305             310                 315                 320

Gly Leu Gly

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Val Tyr Gln Gln Pro Gln Gln Gln Pro Val Ala Gln Ser Tyr Gly
  1               5                  10                  15

Gly Tyr Lys
```